United States Patent [19]

Datta et al.

[11] Patent Number: 4,801,494
[45] Date of Patent: Jan. 31, 1989

[54] NONWOVEN PAD COVER WITH FLUID MASKING PROPERTIES

[75] Inventors: Paul J. Datta, Winnebago County; Gary C. Anderson, Outagamie County; Bernhardt E. Kressner, Winnebago County, all of Wis.

[73] Assignee: Kimberly-Clark Corporation, Neenah, Wis.

[21] Appl. No.: 36,936

[22] Filed: Apr. 10, 1987

[51] Int. Cl.$^4$ .................. A61F 13/16; D04H 3/14; D04H 5/06
[52] U.S. Cl. .................. 428/283; 428/284; 428/286; 428/287; 428/296
[58] Field of Search .......... 428/283, 284, 286, 287, 428/296

[56] References Cited

U.S. PATENT DOCUMENTS

| | | | |
|---|---|---|---|
| 3,886,942 | 10/1975 | Bernardin | 128/290 |
| 4,077,410 | 1/1978 | Butterworth et al. | 128/287 |
| 4,333,979 | 7/1982 | Sciaraffa et al. | 428/179 |
| 4,341,213 | 4/1982 | Cohen | 128/284 |
| 4,472,328 | 11/1984 | Sugimoto et al. | 264/41 |
| 4,483,897 | 9/1984 | Fujimura et al. | 428/288 |
| 4,519,799 | 10/1985 | Sakurai et al. | 604/366 |

FOREIGN PATENT DOCUMENTS

| | | |
|---|---|---|
| 0140560 | 3/1985 | European Pat. Off. . |
| 0164740 | 7/1985 | European Pat. Off. . |
| 0172420 | 8/1986 | European Pat. Off. . |

Primary Examiner—Marion C. McCamish
Attorney, Agent, or Firm—Paul A. Leipold; Thomas J. Connelly

[57] ABSTRACT

A spunbonded liner material having a heavy loading of pigment, formed of a heavier denier than normal spunbonded fiber in a lightweight fabric. In a particularly preferred embodiment, the fibers are formed of polypropylene and the pigment is formed of titanium dioxide present in an amount between about 1 and about 6 percent by weight of the fabric. The fabric material further has an open area of between about 25 and about 50 percent with an average pore size of between about 15,000 and 35,000 square microns and a fiber denier of greater than 3. Masking is greater than two times conventional nonwovens.

10 Claims, 3 Drawing Sheets

FIG. 1A

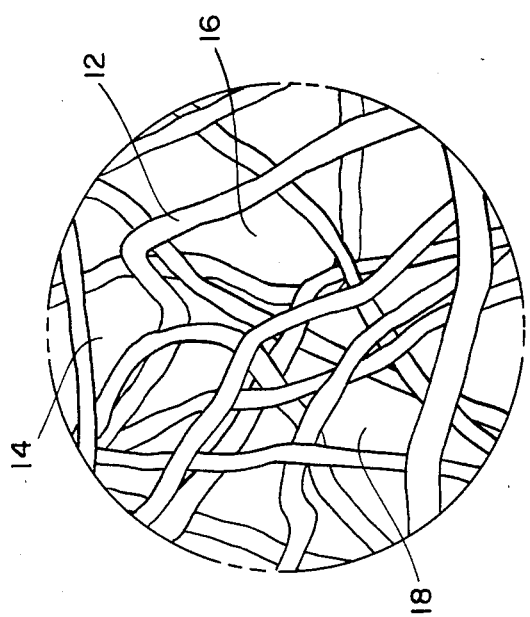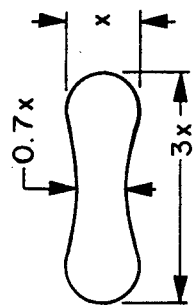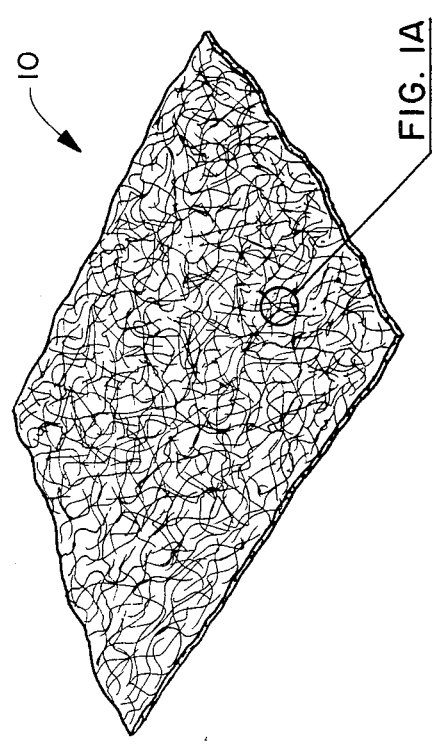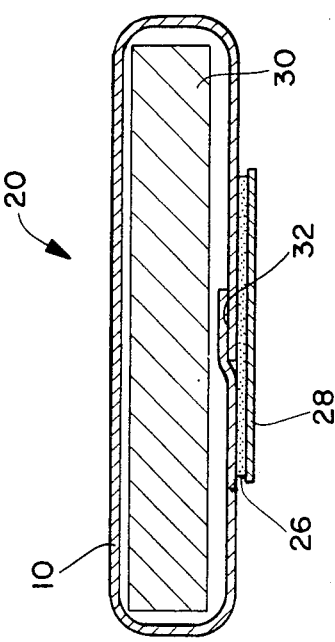
FIG. 1A
FIG. 6
FIG. 1
FIG. 5

NONWOVEN PAD COVER WITH FLUID MASKING PROPERTIES

FIELD OF THE INVENTION

This invention relates to bodyside liner material for products for absorbing human exudate. It particularly relates to materials for the bodyside liners of sanitary napkins.

BACKGROUND OF THE INVENTION

The formation of absorbent garments for use as diapers, incontinent garments or feminine care products has generally involved the combination of an impermeable backing material, a bodyside permeable member and an absorbent placed therebetween. The body exudate placed upon the pad is intended to pass through the liquid permeable layer and be absorbed by the absorbent. The liquid impermeable backing material prevents the exudate from passing through the pad and staining the clothes of the wearer. It has been found that the consumer would prefer not to look at the exudate absorbed by the pad. Therefore, there has been a desire to provide pads for absorption of human exudate with permeable members that will mask exudate that is absorbed within the pad.

It has been proposed the perforated film materials be utilized for the bodyside liners of feminine care pads and diaper garments. Such materials are disclosed in European Patent Application No. 0,039,974. However, these materials have the disadvantage that many users consider them unpleasantly hot and sticky to wear when against the skin. Perforated film materials having a high loading of the opacifying agent and an open area of between 1.3 and 35 percent of the total area of the facing have been disclosed in European Patent Application No. 0,172,420.

Spunbonded materials have been used as cover materials for pads for absorption of human exudate. Spunbonded webs are disclosed in U.S. Pat. No. 3,886,942 - Bernardin. U.S. Pat. No. 4,333,979 - Sciaraffa et al. - suggests the use of titanium dioxide to make a liner sufficiently opaque to cover discoloration. It has also been proposed in U.S. Ser. No. 774,252 filed Sept. 9, 1985 - Van Iten et al. to perforate standard spunbond cover material to increase its ability to pass small clots and improve appearance.

There remains a need for a low weight, large pore liner material that is low in cost, provides good masking of materials absorbed into a pad and is not hot or uncomfortable to the wearer.

Masking is beneficial to the customer by giving a perception of cleanliness. Masking is measured as the reduction in intensity of a black pattern beneath the surface of a pad cover. Masking is measured instrumentally using image analysis equipment.

THE INVENTION

An object of this invention is to overcome disadvantages of prior cover materials.

Another object of this invention is to provide a cover material that will pass a majority of the particulates in menses.

An additional object of the invention is to provide fast absorbency of bodily exudates.

A further object is to provide a pad cover having a dry surface after absorption.

A further additional object is to provide a cover with good hiding of bodily exudates.

These and other objects are generally accomplished by providing a spunbonded liner fabric material having a heavy loading of pigment in fibers of a heavier denier than generally formed into a spunbonded fabric of lightweight. In a particularly preferred embodiment, the fibers are formed of polypropylene and the pigment is titanium dioxide present in an amount between about 1 and about 6 percent by weight. The cover material further has an open area of between about 25 and about 50 percent with an average pore size of between about 15,000 and 35,000 square microns (on pores larger than 50 microns in equivalent circular diameter (ECD)) and an average fiber denier greater than 3. The preferred fabric weight is between about 0.28 and about 0.50 oz. per square yard with or without a surface wetting agent.

BRIEF DESCRIPTION OF THE DRAWINGS

FIG. 1 is a view of a spunbonded web in accordance with the invention.

FIG. 1a is an exploded view of section 1a of FIG. 1.

FIG. 5 is a cross-sectional view of the pad of FIG. 2 on line 5—5 of FIG. 2.

FIG. 6 is a cross-sectional view of a bilobal fiber utilized in the spunbonded material of the invention.

MODES FOR CARRYING OUT THE INVENTION

Figure 2:
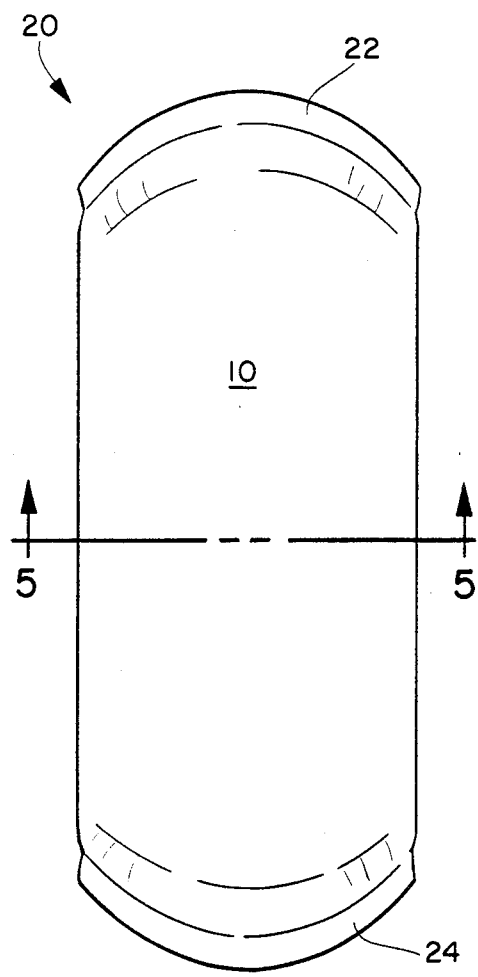
FIG. 2 is a plan view of a sanitary napkin of the invention.
Figure 3:
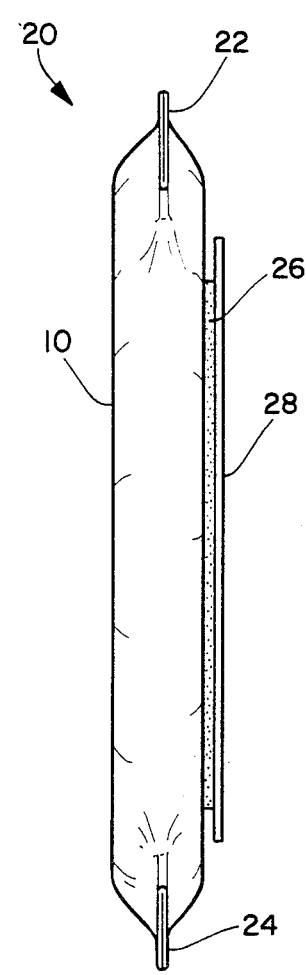
FIG. 3 is a side view of a sanitary napkin of FIG. 2.
Figure 4:
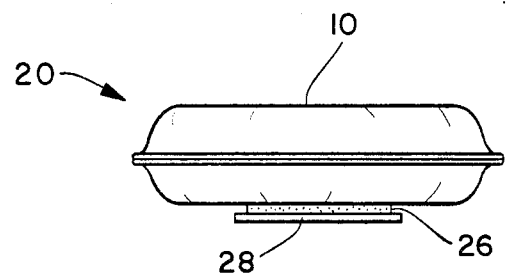
FIG. 4 is the end view of the sanitary napkin of FIG. 2.

The instant invention has numerous advantages over prior cover materials. The cover of the invention is low in cost as it is lightweight and formed of relatively heavy denier spunbonded filaments. The larger filaments are easier to extrude and the lightweight of the web lowers cost as less polymer is used. Further, the relatively large open area allows passing of small clots in menstrual fluid for presenting a cleaner surface. Further, by having a large open area, liquids supplied to the cover are absorbed faster, and the cover both feels and looks drier and cleaner. Additionally, as the cover is formed with a large open area, additional perforating or stretching steps to increase pore area are not necessary. The spunbonded cover of the invention also is soft to the touch and provides good masking of materials absorbed into absorbent pads covered by the cover material of the invention. These and other advantages of the invention will become apparent from the detailed description below.

FIG. 1 and the exploded view of FIG. 1a illustrate a web 10 in accordance with the invention. The web is formed of spunbonded filaments. The spunbonded filaments are formed by extrusion of continuous polymer filaments onto a moving substrate. The filaments are somewhat molten when laid down on the substrate and become adhered to each other at their intersections. It is also possible that the interfiber bonding structure of the spunbonded material may be increased by passing it through heated calender rolls or subjecting it to heated air to aid in fusion between the filaments. It is also possible that the filaments may be united by a binder material. As illustrated in FIG. 1a, the filaments 12 are of fairly thick diameter and have relatively large interstices such as 14, 16 and 18 formed between the filaments.

Illustrated in FIGS. 2–5 is a feminine pad 20 that is provided with the cover of the invention. The permeable cover 10 forms the bodyside of feminine napkin 20. Feminine napkin 20 is sealed at ends 22 and 24. The napkin further is provided with an adhesive 26 covered by a release paper 28. As shown in the cross-section of Figure 5, the feminine pad 20 has absorbent 30 wrapped with the permeable cover 10. The permeable member 10 is overlapped in area 32 where the garment attachment adhesive 26 serves to seal the overlapped area 32 as well as providing garment attachment.

While illustrated with a feminine napkin, the permeable cover of the invention finds use in other devices for absorption of human exudate. Typical of such devices are incontinent garments, bandages, diapers, bed pads and wound dressings. The material may be surfactant treated if desired to aid liquid wetting of the spunbond material. It is preferred for feminine pads that the material be surfactant treated.

The polymer forming the spunbonded material of the invention may be any material that results in a desirable spunbonded product. Typical of such materials are copolymers of polypropylene and polyethylene, linear low-density polyethylene, other polyolefins and polyesters. A particularly preferred material is meltspinnable polypropylene, particularly fiber-grade high-isotactic polypropylene. The polypropylene is preferred as it is low in cost, readily spinnable and provides a good feel to the fabric material formed from the fiber.

It is preferred that the fiber of the invention be provided with a colorant. It is considered that suitable colorants are light pink, peach and other pastel colors. A preferred color is a white color, preferably formed by titanium dioxide. Titanium dioxide is preferred as it is inert, heat stable, very white and easy to process. An alternate white material would be calcium carbonate. The pastel colors may be preferred in some instances to mask certain absorbed materials with a resulting pleasing color.

The fiber diameter of the instant fabric material may be any larger spunbonded diameter that gives good strength, feel and masking or hiding ability. Suitable are fibers of between about 3 and about 15 denier. Preferred for round cross-section fibers are fibers of about 4 to about 6 denier as these have good tactile feel but result in a nonwoven that has a fairly large average aperture size in the material weights utilized. A particularly preferred round fiber has a denier of between about 4.5 and about 5.5 for good tactile feel. In the instance of bilobal fibers, they may suitably be between about 4 and about 15 denier. A preferred bilobal fiber denier is between about 6 and about 10 for a good feel and desired aperture size in the product. The optimum denier for bilobal fibers of polypropylene is considered to be about 6 as these have best tactile feel and hiding power of fluid absorbed. As illustrated in FIG. 6, bilobal fiber has a cross-section that is generally in a dog-bone or hourglass shape.

While the typical cross-sections of fibers are round or bilobal, it is possible that any cross-section could be utilized in the invention.

The nonwoven fabric of the invention may be formed in any average aperture or pore size (larger than 50 microns ECD) which produces the desired hiding power and ability to pass fluids and small clots. A suitable range of average pore size is between about 15,000 and 100,000 square microns. A preferred average pore size (larger than 50 microns ECD) is between about 15,000 and about 35,000 square microns for good menstrual fluid penetration, masking properties and feel. The optimum average pore size is considered to be between about 30,000 and about 35,000 square microns for a fabric that provides good masking of materials absorbed as well as the ability to pass clots and other solid portions through the cover to the absorbent. The average pore size is measured by an image analysis testing procedure.

The titanium dioxide colorant may be present in any desired amount that gives sufficient opacity to the fiber to provide good masking of materials absorbed. The titanium dioxide colorant may suitably be between about 1 and about 6 percent by weight of the finished web. A preferred range is about 3 and about 4 percent for ease of formation, low cost and good hiding or masking ability of the material absorbed.

The fabric forming the permeable cover of the invention may be any desired weight. A preferred weight is between about 0.28 and about 0.5 ounce per square yard for good masking of material absorbed and to provide enough filaments in the cover to provide a uniform look to the nonwoven with large pore size and reasonable strength.

The masking power or hiding power of the nonwoven fabric of the invention is substantially improved from the conventional nonwoven spunbonded materials utilized in many diapers and feminine care products. A measuring system has been established to determine the improvement in masking ability. It has been found that the materials of the invention have a masking improvement of at least 2 and up to about 20 times the masking power of the conventional spunbonded materials.

Figure 7:
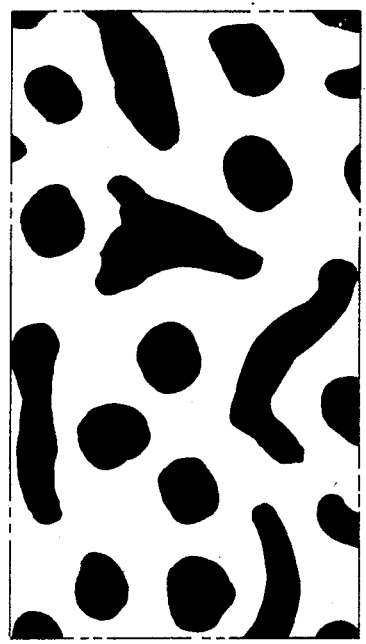
FIG. 7 is an illustration of a black and white test pattern such as used in evaluating masking power.
Figure 8:
FIG. 8 is an illustration of a black and white test pattern covered by a white liner material.
Figure 9:
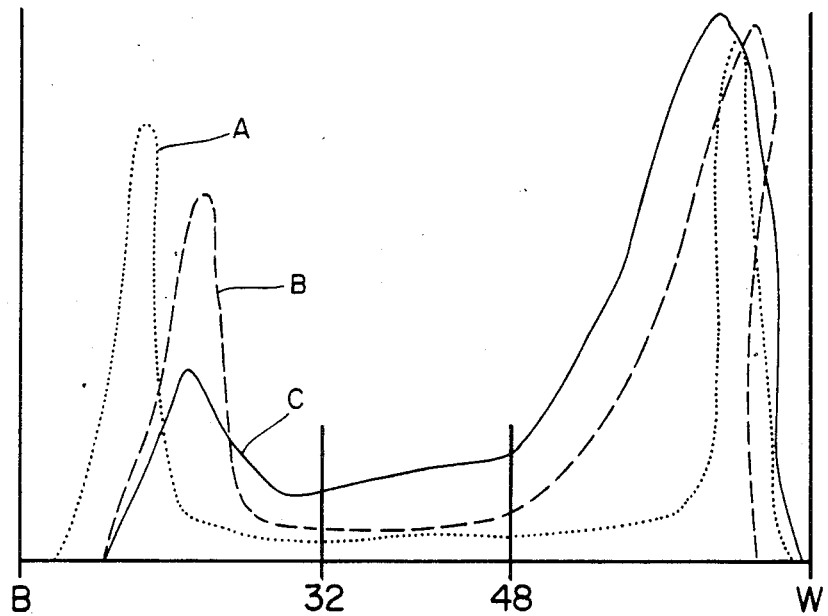
FIG. 9 is a graphic representation of a comparison of masking powers as measured optically.

The method utilized for determining the improvement and hiding powers is illustrated in the accompanying drawing of FIGS. 7, 8 and 9. In FIG. 7, there is illustrated a black and white test pattern. FIG. 8 is an illustration of the black and white test pattern when it is covered with a liner. As can be seen, the test pattern, when covered with the liner, appears gray where the black formerly appeared. A liner with good hiding power has the ability to change most of the black to a gray. The more gray and the less black, then the better the liner. As illustrated in FIG. 9, the liner of the invention is compared with a standard spunbond liner material such as presently utilized on KOTEX TM feminine care products. The left side of the graph indicates the amount of the area that is black. The right is the amount of white. The range of black to white has been divided into 64 equal increments for image analysis. The area between 32 and 48 has been found to be particularly pertinent in establishing of masking power as perceived by a person looking at a covered pattern. It is believed that this is important, as when the gray area from 32 to 48 is significantly increased, the black peak disappears. In this invention description, when it is stated that the masking power is increased two times, it is meant that the area under the curve between 32 and 48 has been doubled from the standard spunbond liner. If the masking power has been increased three times over the standard liner, the area between 32 and 48 of the curve has been tripled. As illustrated in FIG. 9, there are three patterns shown. The uncovered black and white pattern A has, as would be expected, high peaks in he black area and the white area of the graph. The standard spunbond liner, Curve B, has a sizable black peak as well as a large white peak. The Curve C indicating the liner of the invention has more than doubled the area between 32 and 48 and greatly minimized the black peak.

The following examples are intended to be explanatory and not inclusive of all forms of the invention. Parts and percentages are by weight unless otherwise indicated.

EXAMPLE 1

A spunbond, continuous filament polypropylene web is formed as described in Sciaraffa, et al., U.S. Pat. No. 4,333,979, Example I. The polypropylene polymer (i.e., Himont PC-973) is melted in a conventional extruder and spun as continuous filaments through a spinnerette plate. The web is collected at speeds of 700 feet/minute and bonded by hot calendering with a pattern having approximately 27 bonds per square centimeter with a total bond area of 25%±5%. The bonding is accomplished by passing the spunbonded web through the above-mentioned pattern roll and a smooth calender roll. Both rolls are heated to 280° F. The resulting material has the properties found in the following Table I. White pigment (i.e., $TiO_2$) was added via melt addition at a level of 4.5 percent by weight. The material is formed into feminine pads and found to have good ability to pass clots and provide masking of liquid absorbed into the pad. Masking of this web is 5.5 times the masking of a similar web with 1.0% $TiO_2$.

TABLE I

| Example 1 | |
| --- | --- |
| Fiber Cross Section | Round |
| Fiber Denier | 4.5 |
| Basis Weight (oz./yd$^2$) | 0.34 |
| Average Pore Area (sq. microns) | 24,000 |
| Open Area (%) | 45 |
| Pigment Loading (%) | 4.5 |
| Surfactant | no |

EXAMPLE 2

Example 1 is repeated except the extrusion die holes are formed such that the fiber cross-section is bilobal having a shape shown in FIG. 6. As shown in FIG. 6, the bilobal fiber has a cross-section of hourglass or dog bone shape with the long dimension about three times the narrower dimension.

The bonded material is found to have the properties found in the following Table II. The material is formed into feminine pads and found to have good masking ability and a good ability to pass clots.

TABLE II

| Example 2 | |
| --- | --- |
| Fiber Cross Section | Bilobal |
| Fiber Denier | 3.7 |
| Basis Weight (oz/yd$^2$) | 0.39 |
| Average Pore Area (sq. microns) | 17,000 |
| Open Area (%) | 34 |
| Pigment Loading (%) | 4.5 |

TABLE II-continued

| Example 2 | |
| --- | --- |
| Surfactant | no |

EXAMPLE 3

Example 1 is repeated except that the percent $TiO_2$ was 1½, 2½, and 3½. Each material is found to have good masking ability and good ability to pass clots.

EXAMPLE 4

Example 2 is repeated except that the polymer used is linear low density polyethylene (Dow 61800.05). A web with the material properties in Table III is formed. A feminine pad is formed of the web material. The pad is found to exhibit good stain masking and the ability to pass small clots.

TABLE III

| Example 4 | |
| --- | --- |
| Fiber Cross Section | Bilobal |
| Fiber Denier | 4.2 |
| Basis Weight (oz/yd$^2$) | 0.4 |
| Average Pore Area (sq. microns) | 11,300 |
| Open Area (%) | 36 |
| Pigment Loading (%) | 4.5 |
| Surfactant | no |

EXAMPLE 5

Example 1 is repeated except that the denier is increased to 5.5 at a basis weight of 0.42 oz/yd$^2$ and an average pore area of 15,600 (sq. microns). A feminine pad is formed of the web material. The pad is found to exhibit good stain masking and the ability to pass small clots.

While described for primary use as a bodyside cover for pads designed to be used for absorption of human exudate, the nonwoven material of the invention also may be used for other products. Typical of such other uses for which it is suited are the formation of disposable garments such as face masks, operating gowns and drapes. Other uses would be as an agricultural fabric to filter sunlight or provide a mulch. The invention is only intended to be limited by the breadth of the claims attached hereto.

We claim:

1. A permeable nonwoven bodyside cover material for products for absorption of human exudate comprising a pigmented spunbonded web wherein the fibers in said web have a denier of greater than 3 and contain greater than 1 percent colorant and wherein said spunbonded web has an average pore size of about 15,000 to about 100,000 sq. microns, an open area of between about 25 and about 50 percent and a weight of between about 0.28 and 0.5 ounce per square yard.

2. The cover of claim 1 wherein said cover comprises bilobal filaments of between about 4 and about 15 denier.

3. The cover of claim 1 wherein said filament has a round cross-section and a filament denier of between about 4 to about 6.

4. The cover of claim 1 wherein said cover has an open area of between about 30 and about 35 percent.

5. The cover of claim 1 wherein said fibers comprise polypropylene.

6. The cover of claim 1 wherein said fibers comprise between about 1 and about 6 percent by weight titanium dioxide.

7. The cover of claim 1 wherein the average pore size is between about 15,000 and about 35,000 square microns.

8. The cover of claim 1 wherein said filament has a generally round cross-section and an average denier of between about 3 and about 15.

9. A nonwoven material comprising pigmented filaments greater than 3 denier formed into a nonwoven web wherein said nonwoven web has a fabric weight of between about 0.28 and about 0.50 oz/yd$^2$ and a pore size of between about 15,000 and about 30,000 square microns.

10. A pad for absorption of bodily exudate comprising a liquid permeable bodyside nonwoven web, a liquid impermeable backing material and an absorbent therebetween wherein said nonwoven material comprises pigmented filaments of greater than 3 denier formed into a nonwoven web wherein said nonwoven web has a fabric weight of between about 0.28 and 0.50 oz/yd$^2$.

* * * * *